(12) United States Patent
Toth et al.

(10) Patent No.: US 6,904,127 B2
(45) Date of Patent: Jun. 7, 2005

(54) SYSTEM AND METHOD OF MEDICAL IMAGING HAVING DEFAULT NOISE INDEX OVERRIDE CAPABILITY

(75) Inventors: Thomas L. Toth, Brookfield, WI (US); Robert F. Senzig, Germantown, WI (US); Stanley H. Fox, Brookfield, WI (US); Robert Harry Armstrong, Waukesha, WI (US)

(73) Assignee: General Electric Company, Milwaukee, WI (US)

( * ) Notice: Subject to any disclaimer, the term of this patent is extended or adjusted under 35 U.S.C. 154(b) by 559 days.

(21) Appl. No.: 09/683,128

(22) Filed: Nov. 21, 2001

(65) Prior Publication Data

US 2003/0097062 A1 May 22, 2003

(51) Int. Cl.[7] ................................................. H05G 1/34
(52) U.S. Cl. ........................ 378/110; 378/16; 378/108; 378/109
(58) Field of Search ................................. 378/8, 16, 95, 378/98.7, 108–113, 117, 118

(56) References Cited

U.S. PATENT DOCUMENTS

| | | | | |
|---|---|---|---|---|
| 5,379,333 A | | 1/1995 | Toth | |
| 5,400,378 A | * | 3/1995 | Toth | 378/16 |
| 5,450,462 A | | 9/1995 | Toth et al. | |
| 5,485,494 A | * | 1/1996 | Williams et al. | 378/16 |
| 5,696,807 A | | 12/1997 | Hsieh | |
| 5,772,585 A | * | 6/1998 | Lavin et al. | 600/300 |
| 5,822,393 A | * | 10/1998 | Popescu | 378/108 |
| 5,867,555 A | | 2/1999 | Popescu et al. | |
| 6,094,468 A | * | 7/2000 | Wilting et al. | 378/8 |
| 6,178,228 B1 | * | 1/2001 | Schol | 378/162 |
| 6,285,741 B1 | * | 9/2001 | Ackelsberg et al. | 378/110 |
| 6,507,639 B1 | * | 1/2003 | Popescu | 378/108 |

* cited by examiner

*Primary Examiner*—Allen C. Ho
(74) *Attorney, Agent, or Firm*—Ziolkowski Patent Solutions Group, SC; Michael A. Della Penna; Carl B. Horton (57) ABSTRACT

A system and method of medical imaging is designed to reduce a patient's X-ray exposure during scanning. The system automatically generates a default noise index from a received set of scan parameter values that specifies a desired tube current of an X-ray source to use during the scanning of a patient. The default noise index can then be overridden to select a preferred noise index based upon a desired diagnostic quality for a particular volume of interest (VOI) and a diagnostic objective.

37 Claims, 8 Drawing Sheets

SYSTEM AND METHOD OF MEDICAL IMAGING HAVING DEFAULT NOISE INDEX OVERRIDE CAPABILITY

BACKGROUND OF INVENTION

The present invention relates generally to medical imaging and, more particularly, to a system and method of medical imaging having an override capability for a default noise index selection, preferably in computed tomography systems.

Typically, in computed tomography (CT) imaging systems, an X-ray source emits a fan-shaped beam toward an object, such as a patient. The beam, after being attenuated by the patient, impinges upon an array of radiation detectors. The intensity of the attenuated beam radiation received at the detector array is typically dependent upon the attenuation of the X-ray beam by the patient. Each detector element of the detector array produces a separate electrical signal indicative of the attenuated beam received by each detector element. The electrical signals are transmitted to a data processing unit for analysis which ultimately results in the formation of an image.

Generally, the X-ray source and the detector array are rotated with a gantry within an imaging plane and around the patient. X-ray sources typically include X-ray tubes, which conduct a tube current and emit the X-ray beam at a focal point. X-ray detectors typically include a collimator for collimating X-ray beams received at the detector, a scintillator for converting X-rays to light energy adjacent the collimator, and photodiodes for receiving the light energy from the adjacent scintillator.

In one known CT imaging system used to image a volume of interest (VOI), imaging of a patient is conducted by moving the patient through a gantry. Preferably, it is desirable to minimize the patient's exposure to X-rays. To do so, improved signal processing has allowed the use of lower dose CT scans, such as the commercially available 0.5 second CT scanner. Generally, image noise is related to the inverse square root of the dose. However, for different diagnostic objectives and volumes of interest of subjects, higher than needed X-ray exposure doses are known to occur due to the selection of a default noise index which automatically generates a normal default tube current profile. One proposed solution to limit X-ray dosage from the automatically generated tube current profile is to generate an IQ or low dose default tube current profile that automatically generates the default current profile above or below the normal default current profile by a fixed amount. Problems arise, however, when an operator desires to adjust the noise index for the VOI, and in particular, for sub-volumes of the VOI such as when the operator desires to modify X-ray exposure to the subject's sensitive organs, or alternatively when the operator determines that a lower diagnostic quality is sufficient in a sub-volume to achieve the desired patient image.

There is a need for a system that can apply the lowest possible patient dose during imaging by enabling interactive adjustment of an X-ray tube current profile indicative of an applied X-ray dose to the patient. Using existing methods, the setting of a default noise index over the entire VOI may expose a patient to unnecessary X-ray radiation since scanning in certain sub-volumes of the VOI may not require a similar image quality as in other sub-volumes.

Since lower radiation exposure is an on-going goal in X-ray and CT development, it would be desirable to have an imaging system capable of processing pre-scan data to generate a default tube current profile and enabling adjustment of the default tube current profile based on whether a user override is selected.

BRIEF DESCRIPTION OF INVENTION

The present invention provides a system and method of processing imaging data to generate a default tube current profile and enabling adjustment of the default tube current profile based on whether a user override is selected that solves the aforementioned problems.

A system and method of medical imaging is designed to permit adjustment of a patient's X-ray exposure during scanning of an VOI. The system automatically generates a predicted noise index from a received set of scan parameter values that specifies a tube current of an X-ray source for use in scanning a patient. The predicted noise index can then be overridden based on a user override selection that permits adjustment of the predicted noise index according to a desired diagnostic quality for one or more sub-volumes of the VOI and a diagnostic objective.

In accordance with one aspect of the present invention, a method of processing imaging data for a radiation emitting medical imaging device includes the steps of receiving an image application identifier and a set of scan parameter values, and automatically generating a predicted noise index from the received set of scan parameter values. The method also includes the steps of generating an X-ray tube current profile of an X-ray source based at least on the predicted noise index, and allowing user override of the automatically generated predicted noise index by setting a preferred noise index if so selected by a user. If a preferred noise index is set, the method generates a final tube current profile, and acquires imaging data with the final tube current profile.

In accordance with another aspect of the present invention, a method of processing imaging data for a radiation emitting medical imaging device includes the steps of acquiring imaging data of a subject, generating a set of projections for an VOI having a plurality of sub-volumes, and acquiring a target noise index. The method also includes the steps of generating a current profile according to the target noise index, and enabling interactive adjustment of the generated current profile to convey a minimum allowable dose for each sub-volume in the VOI.

In accordance with a further aspect of the invention, a computed tomography system is provided. This system includes a projection source to project towards an object, and a detector to receive high frequency electromagnetic energy attenuated by the object. The detector produces outputs that are transmitted to a data processing system by a plurality of electrical interconnects. The system further includes a computer programmed to construct a plurality of initial projections for an VOI, receive a user input to generate a target noise index, and generate a tube current profile according to the target noise index and a predicted noise index. The computer is further programmed to display the tube current profile on a console such that the tube current profile can be modulated for one or more portions of the VOI. The computer is also programmed to adjust a scan dose for one or more portions of the VOI based on modulation of the tube current, and acquire imaging data for the VOI.

In accordance with yet another aspect of the invention, a computer-readable medium has stored thereon a computer program having a set of instructions that, when executed by a computer, causes the computer to acquire pre-scan data of an VOI of a subject and generate a predicted noise index from the pre-scan data. The computer program also has instructions to generate a tube current profile based upon the predicted noise index and a target noise index, and receive selective adjustments of at least a portion of the tube current profile to adjust a scan dose for a corresponding portion of the VOI based on user analysis of the tube current profile.

In accordance with a further aspect of the present invention, a radiation emitting medical device comprises a means for receiving scan parameters, and a means for adjusting the scan parameters automatically to generate a desired target image quality for a patient. The medical device also includes a means for modifying a tube current profile based on the adjusted scan parameters, and a means for scanning the patient using the modified tube current profile to reconstruct an image of the patient.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

A system and method is described for a computed tomography (CT) system capable of imaging an VOI. It will be appreciated by those of ordinary skill in the art that the present invention is equally applicable for use with different CT system configurations. Moreover, the present invention will be described with respect to the detection and conversion of X-rays. However, one of ordinary skill in the art will further appreciate, that the present invention is equally applicable in other imaging modalities.

Figure 1:
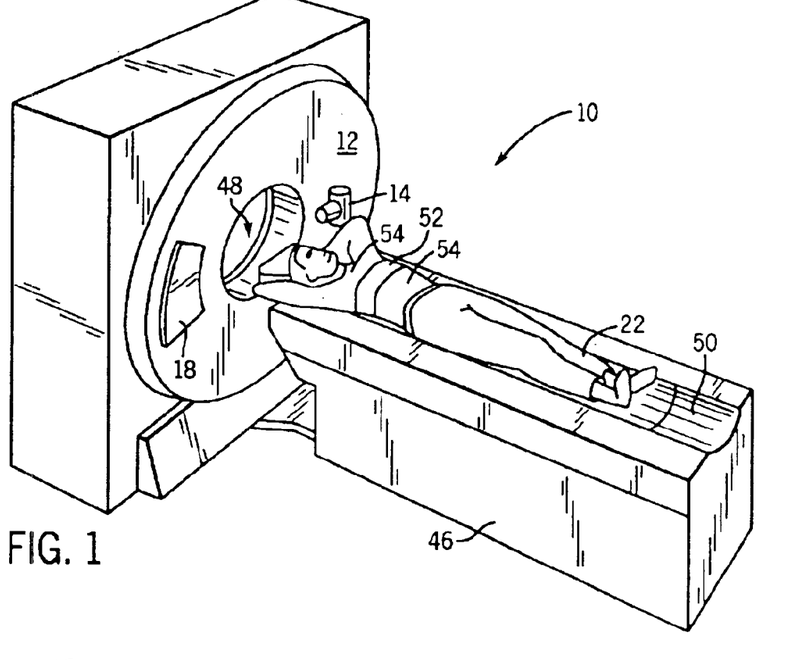
FIG. 1 is a perspective view of a CT imaging system incorporating the present invention.
Figure 2:
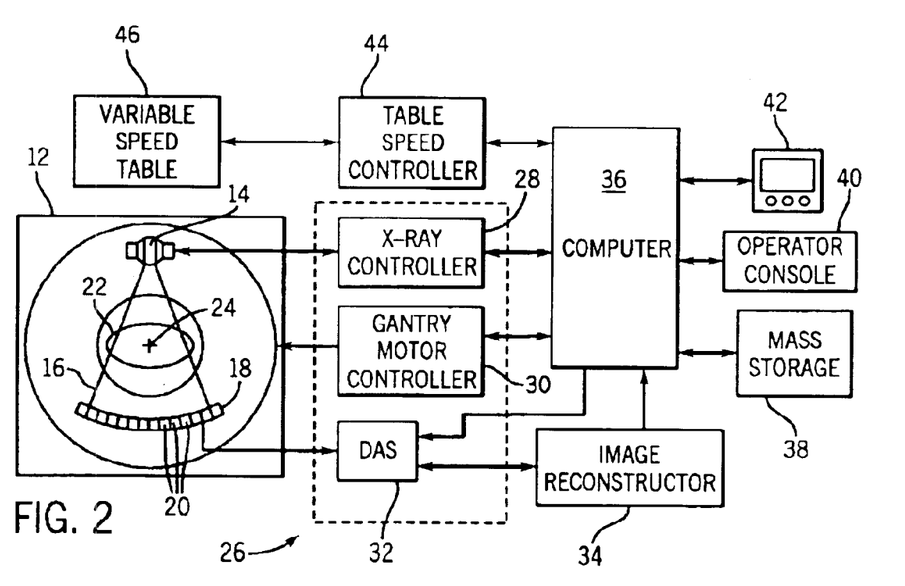
FIG. 2 is a perspective block schematic diagram of the system illustrated in FIG. 1.

Referring to FIGS. 1 and 2, an exemplary computed tomography (CT) imaging system 10 is shown as including a gantry 12 representative of a "third generation" CT scanner. Gantry 12 has an X-ray source 14 that projects a beam of X-rays 16 toward a detector array 18 on the opposite side of the gantry 12. Detector array 18 is formed by a plurality of detectors 20 which together sense the projected X-rays that pass through a medical patient 22. Each detector 20 produces an electrical signal that represents the intensity of an impinging X-ray beam and hence the attenuated beam as it passes through the patient 22. During a scan to acquire X-ray projection data, gantry 12 and the components mounted thereon rotate about a center of rotation 24. Detector array 18 and detectors 20 can be any number of high frequency electromagnetic energy detectors, such as gas-filled, scintillation cell-photodiode, and semiconductor detectors as is know to those skilled in the art of detector design.

Rotation of gantry 12 and the operation of X-ray source 14 are governed by a control mechanism 26 of CT system 10. Control mechanism 26 includes an X-ray controller 28 that provides power and timing signals to an X-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized X-ray data from DAS 32 and performs high-speed reconstruction. The reconstructed image is applied as an input to a computer 36 which stores the image in a mass storage device 38.

Computer 36 also receives commands and scanning parameters from an operator via console 40 that has a keyboard for entering commands and scanning parameters. An associated cathode ray tube display 42 allows the operator to observe the reconstructed image and other data from computer 36. The operator supplied commands and parameters are used by computer 36 to provide control signals and information to DAS 32, X-ray controller 28 and gantry motor controller 30. In addition, computer 36 operates a table speed controller 44 which controls a variable speed table 46 during imaging of a patient 22 within gantry 12. Particularly, table 46 is configured to move a patient 22 through a gantry opening 48 along an axis 50, and may include a single or multiple speed settings.

In operation, a patient 22 or object is positioned within the CT scanner or imaging device 10 on the table 46 with a selected volume of the patient chosen for scanning adjacent to the gantry 12. A technician or health-care operator enters input into the operator console 40, thereby defining an VOI or scanning volume such as a thorax of the patient 22, which includes a cardiac volume 52 and a pair of non-cardiac volumes 54. The computer 36 then instructs the table speed controller 44 to move the table 46 towards the gantry opening 48 causing the patient 22 to enter the gantry opening 48. Control mechanism 26 causes X-ray controller 28 to provide power and timing signals to X-ray source 14 while the gantry motor controller 30 causes rotation of gantry 12 to conduct an imaging scan of the patient 22 passing through the gantry 12. While scanning the VOI, detectors 20 send the X-ray data acquired to DAS 32 and image reconstructor 34 for digitalization and image reconstruction. Computer 36 then processes the digitized X-ray data to provide a reconstructed image of the VOI on display 42. If desired, the operator can also initiate a pre-scan of the medical patient or subject to acquire pre-scan imaging data. A scout scan can then be generated for the pre-scan imaging data and displayed on console 40. Additionally, a default tube current profile capable of being modulated and based on an operator selected diagnostic quality may also be displayed on the console 40 according to the steps and/or acts discussed with respect to FIGS. 3–9.

Figure 3:
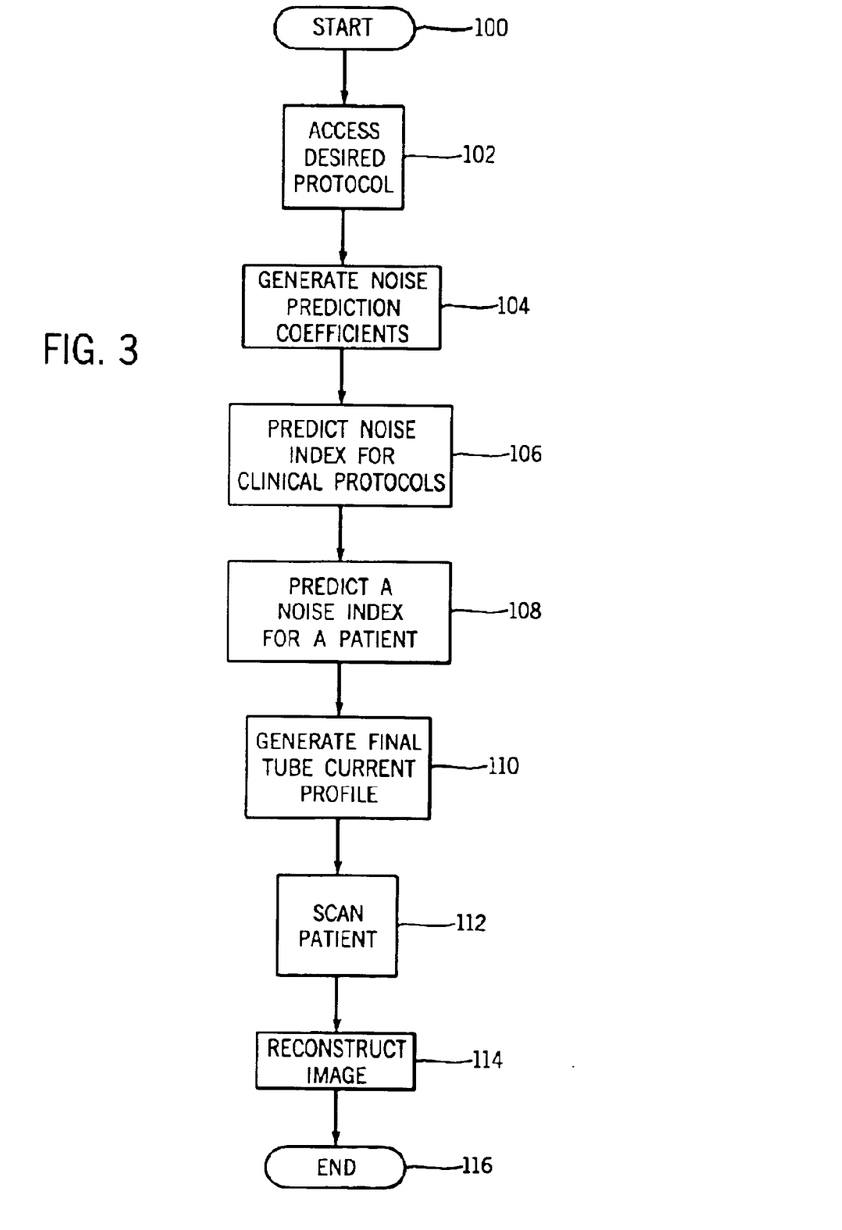
FIG. 3 is a flow chart showing a process of the present invention and implemented in the system of FIGS. 1 and 2.

Referring to FIG. 3, a flowchart illustrating the steps of a method and acts associated with a computer program in accordance with the present invention implemented in the system of FIGS. 1 and 2 is shown. The method and/or computer program is initiated at 100 by a technician or CT scanner operator who provides input into the computer to access desired protocol 102, and select or generate noise prediction coefficients 104 for a patient or object to be imaged. Generally, such operator-entered input can include defining an VOI for a particular anatomy, wherein the VOI has a starting position and an ending position along a common axis, such as axis 50 of FIG. 1, for conducting a scan of the patient to reconstruct an image. Other operator-input can include selection of a target noise index, an image application identifying a type of scan, and a set of scan parameter values, such as slice thickness, for the selected scan type. A predicted noise index profile for clinical protocols is then determined from the selected scan parameter values at 106, and the method and/or program predicts a noise index for a patient 108. After predicting the noise index 108, the method and/or computer program proceeds to generate a final tube current profile 110, which varies depending on whether an operator or user chooses to override a default or predicted tube current profile for imaging the VOI.

The tube current profile predicts an electric current amperage passing though an X-ray source for each sub-volume of the VOI to perform an imaging scan of a patient. The profile is at least partially based on one or more determined noise index values and indicates a lowest possible dose of X-rays to the patient to maintain a consistent image quality. An operator may determine to override either directly or by other methods the tube current profile based on a number of factors. One factor, for example, is patient anatomy which has different image quality needs. That is, the patient anatomy may require operator interaction to vary the dose in sub-volumes of the VOI where noise artifacts interfere with image quality.

After selection of a final tube current 110 derived from the predicted noise index from the patient and the desired noise index based on user override of the predicted noise index, the patient is scanned 112 to acquire image data. The method and/or computer program uses the acquired imaging data to reconstruct an image of the patient 114, which can be displayed on a console or other display device, and the method ends at 116.

Figure 4:
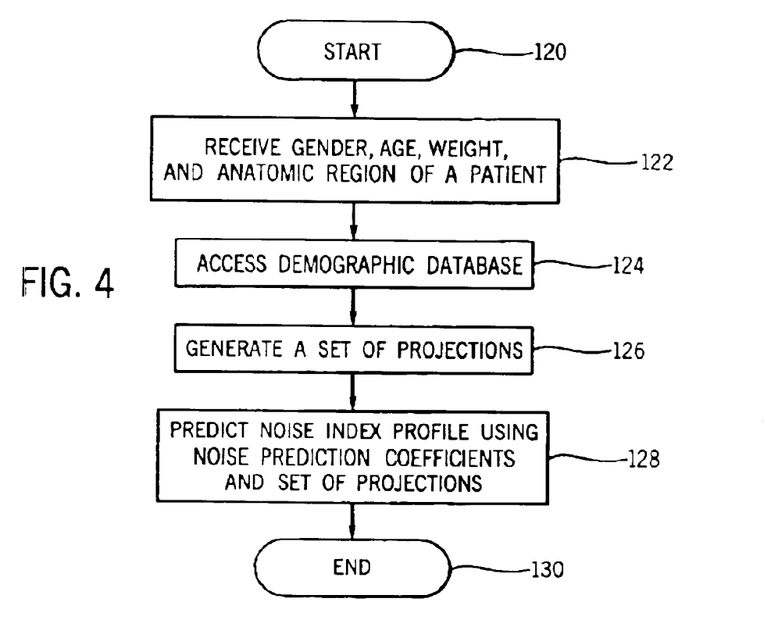
FIG. 4 is a flow chart showing a process of predicting a noise index.

Referring now to FIG. 4, one method of predicting a noise index starts at 120. An operator enters patient data representing gender, age, weight, and anatomic volume of the patient which is processed by the computer 122. The computer accesses a patient demographic database 124, which stores data for constructing projection sets based on the operator input of patient data. The computer uses the stored data to generate a set of initial projections 126 having a plurality of sub-volumes for the specified patient. If desired, the set of initial projections can be displayed on the console 40 of FIG. 2.

After generating the set of projections 126, an image noise or noise index profile is predicted 128 for the patient using the noise prediction coefficients 102 of FIG. 3 and the generated set of projections 126. The method then ends 130, and a noise index profile is predicted that can be used to generate a tube current profile to achieve a desired noise index.

Figure 5:
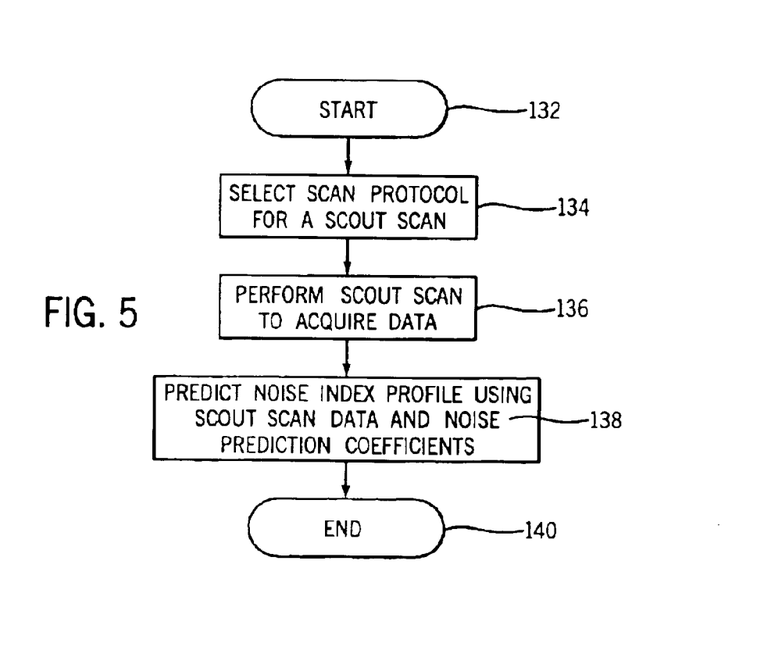
FIG. 5 is a flow chart showing another process of predicting a noise index.

FIG. 5 is a flow chart showing another process of predicting a noise index profile for the patient. The process begins at 132 whereupon an operator enters scan parameter to select a scan protocol for a scout scan 134. The scout scan is performed and data is acquired 136. After acquiring data from the scout scan 136, the data and the generated noise prediction coefficients 102 of FIG. 3 are used to predict the noise index profile 138. The method then ends at 140, and the predicted noise index profile can again be used to generate a tube current profile to achieve a desired noise index.

Figure 6:
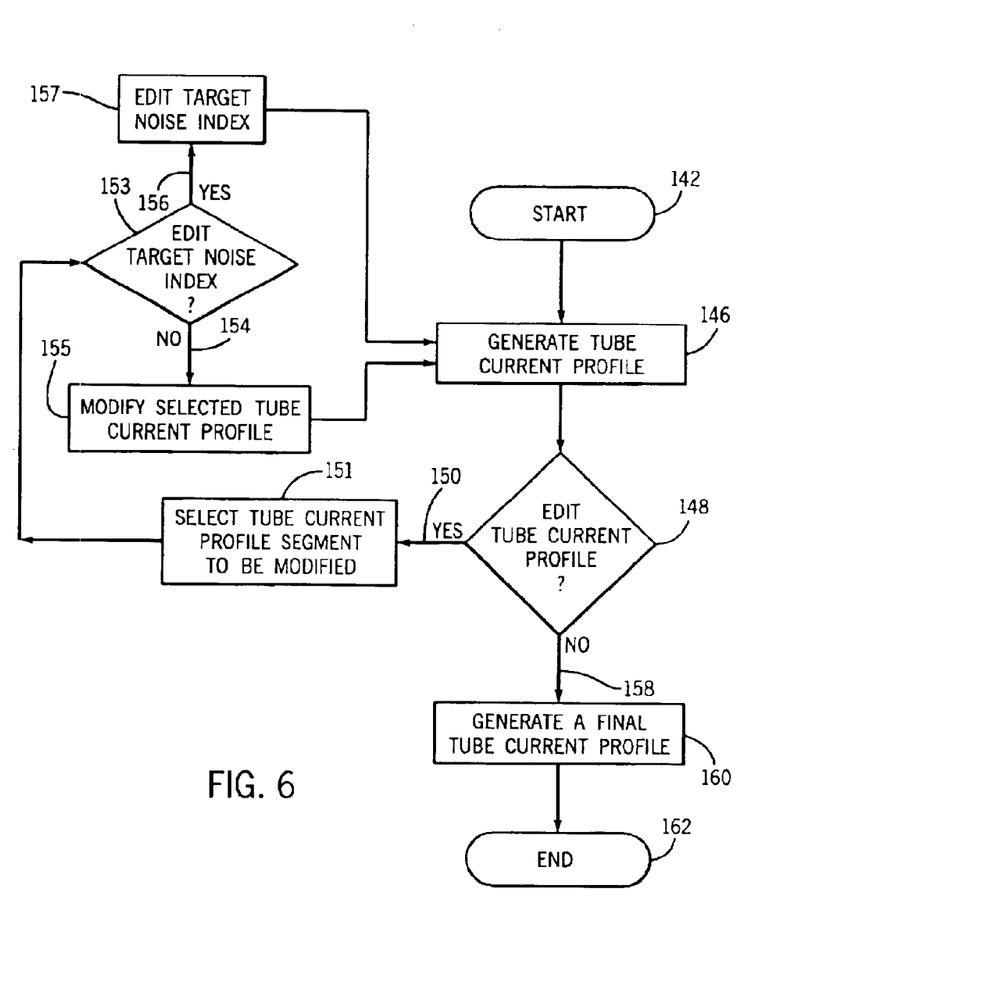
FIG. 6 is a flow chart showing a process of generating a final tube current profile for the selected noise index of FIG. 3.

Referring to FIG. 6, one method and/or computer program configured to enable direct entry by an operator to select the noise index 110 of FIG. 3 starts at 142. A selected noise index input is directly entered by an operator to generate a tube current profile at 146 from the predicted noise index profile for the patient. Selection of the noise index by the operator can be based on the operator's experience of a preferred target noise index for a particular scan type, diagnostic quality requirements, and/or the VOI. After generation of the tube current profile 146, a decision is made whether to edit the tube current profile 148 using user override. If user override is selected 150, a tube current profile segment to be modified is selected 151, and a query whether to edit the target noise index is made 153. If the target noise index is not edited 154, the selected tube current profile is modified directly 155 and a new tube current profile is generated at 146 based on the edited segments. If the target noise index is edited 156, the method and/or computer program edits the target noise index for the subset 157, and a new tube current profile is generated at 146.

Editing of either the entire tube current profile or one or more subsets continues until a desired noise index and tube current profile is selected for the VOI. Editing can be accomplished by an operator interactively modulating either the entire tube current profile or a portion of the profile. Modulation can occur on a graphical user interface, or alternatively by direct entry selection of tube current values for sub-volumes of the VOI. Once the desired tube current is determined, editing of the tube current profile is not selected 158 and a final tube current profile is generated 160. Preferably, the final tube current profile is edited to lower the tube current and reduce X-ray exposure to the patient in volumes where a lower image quality is sufficient and/or the diagnostic objective permits a lower dose. The method and/or computer program then ends at 162.

Figure 7:
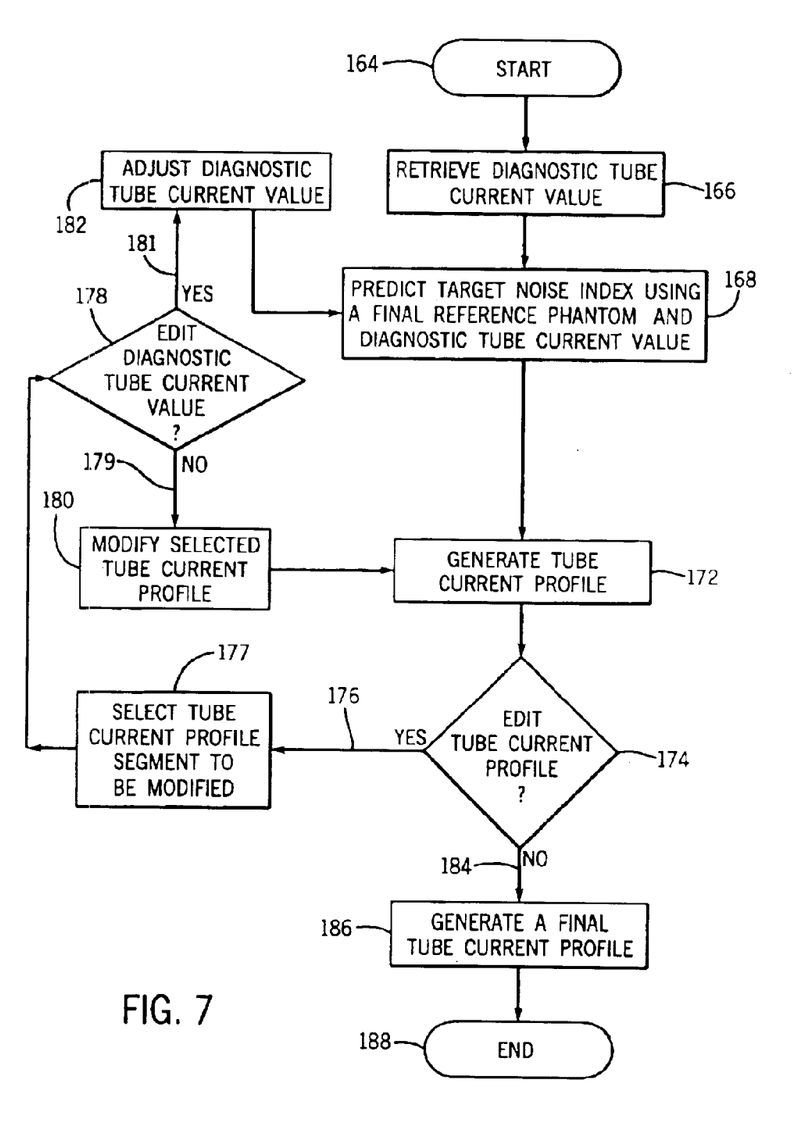
FIG. 7 is a flow chart showing a process of predicting a noise index and generating a final tube current profile using a phantom for the selected noise index of FIG. 3.

FIG. 7 is a flow chart of another embodiment of tho present invention for predicting and selecting a target noise index. Selection of the target noise index begins at 164 wherein a diagnostic tube current input method and/or computer program is retrieved from a stored clinical protocol 166. A target noise index is generated using a final reference phantom and a diagnostic tube current value 168. The data from the reference phantom can vary according to a selected projection area of the phantom and an oval ratio indicative of the ratio of projection measures taken at zero and ninety degree gantry rotation positions.

A tube current profile is generated at 172 from the predicted noise index for the patient. The tube current profile is indicative of a predicted low dose X-ray exposure to the patient based on the entered diagnostic tube current value and reference phantom. After generation of the tube current profile 172, a decision is made whether to edit the tube current profile 174 using user override. If user override is selected 176, then the operator selects the tube current profile segment to be modified 177. The method and/or computer program proceeds to decide whether to edit the diagnostic tube current value 178. If editing of the diagnostic tube current value is not selected 179, the selected tube current profile is modified at 180 and a new tube current profile is generated at 172. If editing of the diagnostic tube current value is selected 181, the diagnostic tube current value is adjusted 182 and a new target noise index is generated at 168 to produce a new tube current profile 172.

Editing of either the entire tube current profile or one or more subsets continues until a desired noise index and tube current profile is created for the VOI. Once the desired tube current is determined, editing of the tube current profile is not selected 184 and a final tube current profile is generated at 186. Once again, the final tube current profile is preferably edited to lower the tube current and reduce X-ray exposure to the patient in volumes where a lower image quality is sufficient and/or the diagnostic objective permits a lower dose. The method and/or computer program then ends at 188.

Figure 8:
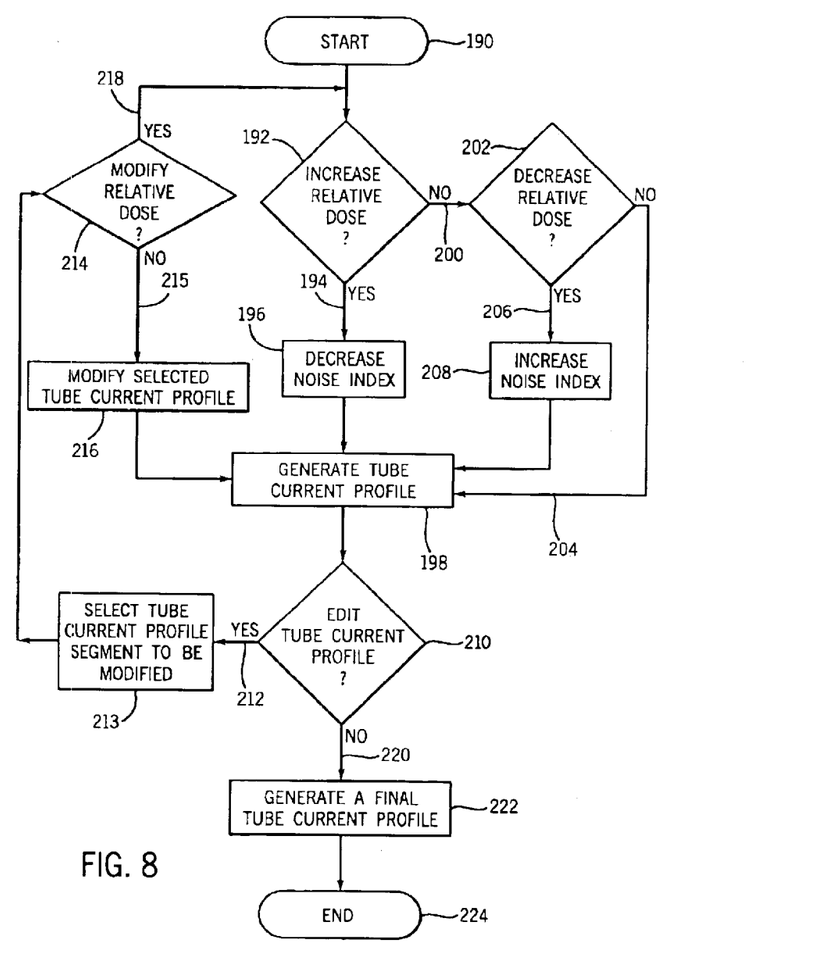
FIG. 8 is a flow chart showing another process of generating a final tube current profile for the selected noise index of FIG. 3.

Referring now to FIG. 8, a flow chart of another method and/or computer program for selecting a noise index begins at 190. A decision to increase the relative dose occurs at 192, and if so 194, an operator may increase the relative dose which causes a decrease in the noise index 196. Once the noise index is set, a tube current profile is generated at 198.

If the relative dose is not increased 200, a decision to decrease the relative dose 202 occurs. If the relative dose is not decreased 204, then the tube current profile is generated based on the pre-selected target noise index. Otherwise, the relative dose is decreased 206 and the noise index is increased 208. The method and/or computer program uses the increased noise index to generate the tube current profile at 198.

After generation of the tube current profile 198, a decision similar to the other noise selection processes is made concerning whether to edit the tube current profile 210 using user override. If user override is selected 212, then the operator selects one or more tube current profile segments to modify 213 and a query to modify the relative dose is determined 214. If the relative dose is not modified 215, the selected tube current profile is modified 216 and a new tube current profile is generated at 198. If the relative dose is modified 218, the method and/or computer program loops to the beginning and again determines whether to increase the relative dose at 192.

Editing of either the entire tube current profile or one or more subsets continues until a desired noise index and tube current profile is created for the VOI. Once the desired tube current is determined, editing of the tube current profile is not selected 220 and a final tube current profile is generated at 222. As with the other noise index selection processes, the final tube current profile is preferably edited to lower the tube current and reduce X-ray exposure to the patient in volumes where a lower image quality is sufficient and/or the diagnostic objective permits a lower dose. The method and/or computer program then ends at 224.

FIGS. 6–8 indicate methods and/or computer programs acts that enable interactive adjustment of the generated tube current profile to convey a minimum allowable dose for each sub-volume in the VOI, and generate a final tube current profile to produce a selected noise index. Each of these methods and/or acts that apply user analysis to generate the final tube current profile, however, can be further modified in accordance with the steps of FIG. 9.

Figure 9:
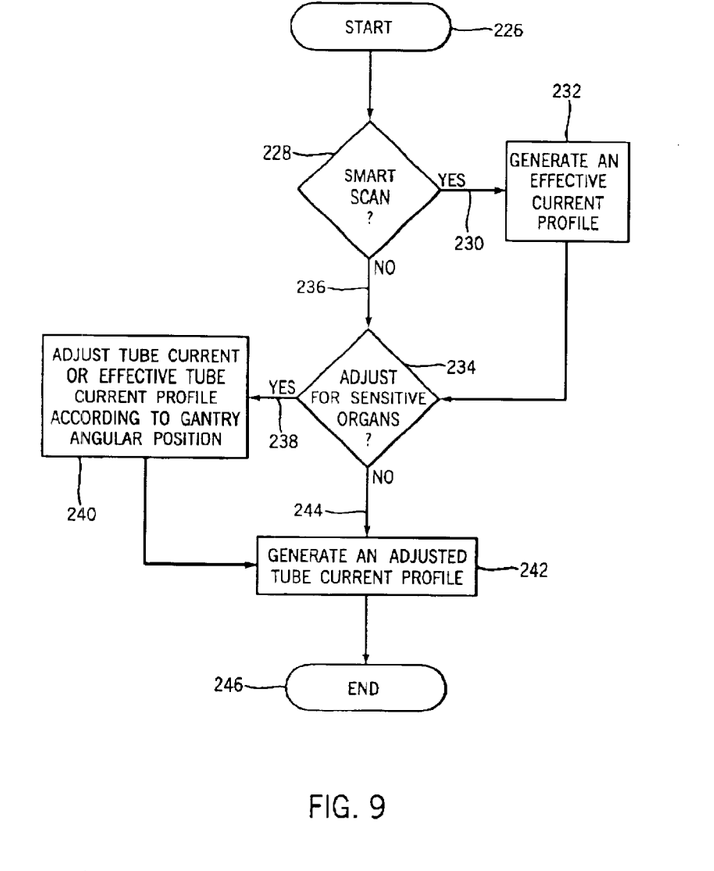
FIG. 9 is a flow chart showing a process of adjusting the final tube current profile to generate an adjusted tube current profile.

Referring to FIG. 9, the method and/or computer program begins at 226, wherein a final tube current profile is generated. Next, a decision block queries whether to enable smart scan at 228. Smart scan is a process wherein an X-ray dose is varied with the gantry angle to account for patient asymmetry. If smart scan is selected 230, an effective tube current profile is generated 232. The effective tube current profile can be plotted on a graphical user interface or displayed as a set of data for operator modulation of the tube current profile. After generating an effective tube current profile, a decision to adjust for sensitive organs 234 is made. If smart scan is not selected 236, the method and/or computer program immediately proceeds to decide whether to adjust for sensitive organs at 234.

Depending on the type of scan, desired diagnostic quality, VOI, and other factors, an operator may desire to limit the X-ray exposure to certain anatomical volumes sensitive to radiation, such as the eyes, ovaries, breasts, and gonads. If adjustment is desired 238, the tube current or effective tube current profile is adjusted according to the gantry angular position 240 to lower X-ray exposure to sensitive organs when the X-ray source is closest to each of the sensitive organs. That is, during each gantry rotation the tube current decreases as the gantry is positioned above a sensitive organ, such as the eyes of a patient, and increases as the gantry rotates behind the patient's head. After the tube current adjustment 240, the method and/or computer program generates an adjusted tube current profile at 242 which is used to generate the selected noise index. If no adjustment for sensitive organs is desired 244, the adjusted tube current profile is again generated at 242 and the method and/or computer program ends at 246.

Figure 10:
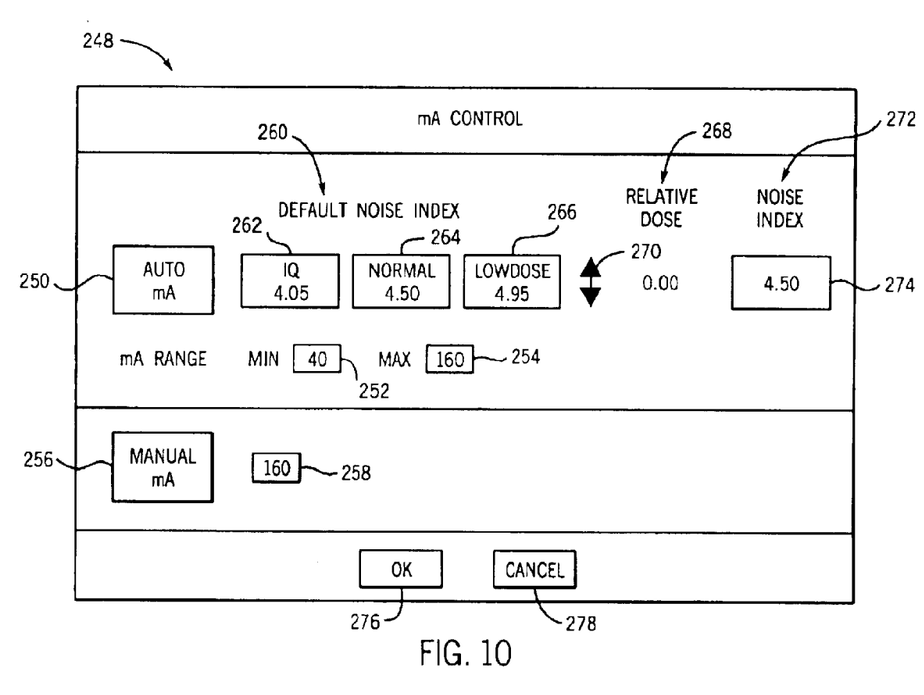
FIG. 10 is an exemplary computer user interface for selecting the noise index.

Referring now to FIG. 10, one exemplary graphical user interface 248 configured to permit operator control of a tube current profile is shown. An operator can select automatic tube current generation 250, and specify a range of tube current values between a minimum value 252 and a maximum value 254 that the tube current can be between. Alternatively, the operator can select manual tube current generation 256 and specify a desired tube current value 258.

A default noise index 260 is generated by selecting one of the IQ 262, normal 264, and lowdose 266 selections. The IQ selection 262 provides an X-ray tube current profile having tube current values a fixed amount higher than the normal dose 264, which is a fixed amount above the lowdose selection 266. If desired, the relative dose 268 or noise index values can be increased or decreased by adjustment selectors 270. In a preferred embodiment, the adjustment selectors are configured to change the noise index in five percent increments, although other incremental or continuous adjustments are contemplated with the present invention. Alternatively, the noise index 272 may be directly modified by entering a direct input at 274. Upon choosing the OK selection 276, the final tube current profile is created. If improper data is entered, or an operator prefers to enter a new set of data, the cancel selection 278 may be utilized to reselect generation of the tube current profile.

Although FIG. 10 shows one computer user interface method for editing and generating a tube current profile, other configurations known to those skilled in the art are contemplated and within the scope of the present invention.

In accordance with one aspect of the present invention, a method of processing imaging data for a radiation emitting medical imaging device, such as a CT scanner includes the steps of receiving an image application identifier and a set of scan parameter values, and automatically generating a predicted noise index from the received set of scan parameter values. The method also includes the step of generating an X-ray tube current profile based at least partially on the predicted noise index if so selected by a user. If a preferred noise index is set, the method generates a final tube current profile and acquires imaging data with the final tube current profile.

In accordance with another aspect of the present invention, a method of processing imaging data for a radiation emitting medical imaging device includes the steps of acquiring imaging data of a subject, such as a patient or object, and generating a set of projections for an VOI having a plurality of sub-volumes. The method also acquires a target noise index, which may be acquired using a scout scan. The method further includes the steps of generating an X-ray current profile according to the target noise index, and enabling interactive adjustment by a user of the generated current profile to convey a minimum allowable dose for each sub-volume in the VOI.

In accordance with a further aspect of the invention, a computed tomography system is provided. This system includes a projection source to project towards an object, and a detector to receive high frequency electromagnetic energy attenuated by the object. The detector produces outputs that are transmitted to a data processing system by a plurality of electrical interconnects. The system also includes a computer programmed to construct a plurality of initial projections for an VOI and receive a user input to generate a target noise index. The computer is also programmed to generate a tube current profile according to the target noise index and a predicted noise index, and display the tube current profile on a console such that the tube current profile can be modulated for one or more portions of the VOI. The tube current profile can be displayed as a set of data values, or alternatively as a graphical user interface. The computer is further programmed to adjust a patient X-ray dose for one or more portions of the VOI based on modulation of the tube current, and acquire imaging data for the VOI.

In accordance with yet another aspect of the invention, a computer-readable medium having stored thereon a computer program having a set of instructions that, when executed by a computer, causes the computer to acquire pre-scan data of an VOI of a subject and generate a predicted noise index from the pre-scan data. The computer program also has instructions to generate an X-ray tube current profile based upon the predicted noise index and a target noise index, and receive selective adjustments by an operator of at least a portion of the tube current profile. The selective adjustments are configured to adjust a scan dose for a corresponding portion of the VOI based on user analysis of the tube current profile.

In accordance with a further aspect of the present invention, a radiation emitting medical device comprises a means for receiving scan parameters, and a means for adjusting the scan parameters automatically to generate a desired target image quality for a patient. The medical device also includes a means for modifying a tube current profile based on the adjusted scan parameters, and a means for scanning the patient using the modified tube current profile to reconstruct an image of the patient.

The present invention has been described in terms of the preferred embodiment, and it is recognized that equivalents, alternatives, and modifications, aside from those expressly stated, are possible and within the scope of the appending claims.

What is claimed is:

1. A method of processing imaging data for a radiation emitting medical imaging device, the method comprising:
receiving an image application identifier;
receiving a set of scan parameter values;
automatically generating a predicted noise index from the received set of scan parameter values;
generating an X-ray tube current profile based at least on the predicted noise index;
allowing user override of the automatically generated predicted noise index based on the X-ray tube current profile and setting a preferred noise index if so selected by a user, and if a preferred noise index is set, generating a final tube current profile; and
acquiring imaging data with the final tube current profile.

2. The method of claim 1 wherein the step of determining the preferred noise index further comprises the step of adjusting the automatically generated predicted noise index according to a direct user input.

3. The method of claim 2 wherein the direct user input defines a target noise index for scanning and processing an image.

4. The method of claim 1 further comprising the steps of:
initiating a pre-scan of a subject;
acquiring pre-scan imaging data;
generating a scout image from the pre-scan imaging data;
displaying the scout image; and
displaying a tube current profile for a selected diagnostic quality, wherein one or more portions of the tube current profile are adjustable.

5. The method of claim 1 further comprising the step varying the automatically determined predicted noise index according to a diagnostic current input.

6. The method of claim 1 wherein the step of automatically generating a predicted noise index further comprises the steps of:
receiving patient input;
accessing a patient demographic database;
generating a set of projections; and
predicting an image noise based on the generated set of projections.

7. The method of claim 6 wherein the patient input includes gender, age, weight, and anatomical volume data of a patient.

8. The method of claim 1 wherein the step of automatically generating a predicted noise index further comprises the steps of:
receiving a diagnostic tube current value; and
predicting a noise index using a phantom reference and the diagnostic tube current value.

9. The method of claim 1 wherein the step of automatically generating a predicted noise index further comprises the steps of:
performing a scout scan to acquire pre-scan data; and
predicting a noise index using acquired pre-scan data.

10. The method of claim 1 wherein the preferred noise index is adjustable for sub-volumes in an VOI.

11. The method of claim 1 further comprising the step of varying a patient dose during a rotation of an x-ray source for one or more sensitive organ sub-volumes in an VOI.

12. A method of processing imaging data for a radiation emitting medical imaging device, the method comprising:
acquiring imaging data of a subject;
generating a set of projections for an VOI having a plurality of sub-volumes;
acquiring a target noise index;
generating a tube current profile for a radiation emitting tube according to the target noise index; and
enabling interactive adjustment of the generated tube current profile to convey a dose specific for each sub-volume in the VOI such that diagnostic quality is variable across the VOI.

13. The method of claim 12 further comprising the step of varying an application of a patient dose for each rotation of an X-ray source within a sub-volume in the VOI to limit X-ray exposure to sensitive organs of a patient.

14. The method of claim 13 further comprising the step of generating an effective tube current profile based on the varied patient dose for each gantry rotation and plotting the effective tube current profile on a graphical user interface.

15. The method of claim 12 further comprising the step of plotting the tube current profile on a graphical user interface.

16. The method of claim 15 wherein user modulation of a portion of the plotted tube current profile on the graphical user interface causes the noise index to vary for the portion of the tube current profile modulated.

17. The method of claim 12 further comprising the step of adjusting at least one of a noise index and a relative dose index to acquire the imaging data of the subject.

18. The method of claim 12 wherein the step of interactively adjusting includes a direct adjustment of a noise index to acquire the imaging data of the subject.

19. The method of claim 12 wherein the step of generating a set of projections includes the steps of:
receiving a patient input; and
accessing a patient demographic database.

20. A computed tomography system comprising:
a high frequency electromagnetic energy projection source to project high frequency energy towards an object;
a detector to receive high frequency electromagnetic energy attenuated by the object;
a plurality of electrical interconnects configured to transmit detector outputs to a data processing system; and
a computer programmed to:
construct a plurality of initial projections for an VOI;
receive a user input to generate a target noise index;
generate a tube current profile for the high frequency electromagnetic energy projection source according to the target noise index and a predicted noise index;
display the tube current profile on a console wherein the tube current profile can be modulated for one or more portions of the VOI;
adjust a scan dose for one or more portions of the VOI based on user modulation of the tube current profile; and
acquire imagine data for the VOI.

21. The system of claim 20 wherein the computer is further programmed to display the plurality of initial projections on the console.

22. The system of claim 21 wherein the computer is further programmed to:
generate an effective tube current profile indicating a lower X-ray dose to a patient based on the asymmetry of the patient; and
display a graphical representation of the effective tube current profile on the console.

23. The system of claim 20 wherein the computer is further programmed to modulate the tube current profile based on a direct user target noise input for selected volumes of the VOI.

24. The system of claim 20 wherein the computer is further programmed to define the tube current profile by accessing a patient demographic database storing patient gender, age, weight, and anatomical data therein.

25. The system of claim 20 wherein the computer is further programmed to vary the tube current profile as a function of a gantry angle.

26. A computer-readable medium having stored thereon a computer program having a set of instructions that, when executed by a computer, causes the computer to:
acquire pre-scan data of an VOI of a subject;
generate a predicted noise index from the pre-scan data;
generate a tube current profile for a radiation source designed to project radiation at a subject during data acquisition based upon the predicted noise index and a target noise index; and
receive selective adjustments of at least a portion of the tube current profile to adjust a scan dose for a corresponding portion of the VOI based on user analysis of the tube current profile.

27. The computer-readable medium of claim 26 wherein the set of instructions further causes the computer to generate a visual display of the tube current profile and a scout image of the subject.

28. The computer-readable medium of claim 27 wherein the set of instructions further causes the computer to generate an effective tube current profile and graphically plot the effective tube current profile to display a lower tube current capable of generating an image of the subject.

29. The computer-readable medium of claim 26 wherein the subject includes a medical patient and the set of instructions further causes the computer to reduce dosage for acquiring imaging data of anatomical volumes sensitive to radiation, the anatomical volumes including eyes, ovaries, breasts, and gonads.

30. The computer-readable medium of claim 26 wherein incrementally varying a relative noise index adjusts the tube current profile.

31. The computer-readable medium of claim 26 wherein the set of instructions further causes the computer to adjust the tube current profile upon direct entry of a selected noise index by an operator.

32. A radiation emitting medical device comprising:
means for receiving scan parameters;
means for adjusting the scan parameters automatically to generate a desired target image quality across a VOI for a patient;
means for modifying a radiation tube profile based on the adjusted scan parameters to account for sub-volumes of elevated interest such that radiation dose to the sub-volumes of elevated interest exceeds that of other sub-volumes of the VOI; and
means for scanning the patient using the modified radiation tube current profile to reconstruct an image of the patient with image quality for the sub-volumes of elevated interest exceeding that of the other sub-volumes of the VOI.

33. The medical device of claim 32 wherein the target image quality is determined by a target image noise index.

34. The medical device of claim 32 wherein the target image quality is determined by a diagnostic tube current and one of a reference phantom and a demographic database.

35. The medical device of claim 32 wherein the means for modifying a tube current profile includes one of graphical adjustment and direct entry adjustment.

36. The medical device of claim 32 wherein the means for modifying a tube current profile includes a means for modifying only a portion of the tube current profile.

37. The medical device of claim 32 wherein the means for modifying a tube current profile includes a means for modifying the tube current in sensitive organ regions for each gantry rotation.

* * * * *